United States Patent [19]

Maroni et al.

[11] Patent Number: 5,306,683
[45] Date of Patent: Apr. 26, 1994

[54] TRANSITION METAL SULFIDE LOADED CATALYST

[75] Inventors: Victor A. Maroni, Naperville; Lennox E. Iton, Downers Grove; James W. Pasterczyk; Markus Winterer, both of Westmont; Theodore R. Krause, Lisle, all of Ill.

[73] Assignee: ARCH Development Corporation, Chicago, Ill.

[21] Appl. No.: 877,308

[22] Filed: May 1, 1992

[51] Int. Cl.⁵ .............................................. B01J 29/08
[52] U.S. Cl. ...................................... 502/60; 502/65; 502/79
[58] Field of Search ........................ 502/60, 79, 62, 65

[56] References Cited

U.S. PATENT DOCUMENTS

| | | | |
|---|---|---|---|
| 2,971,824 | 2/1961 | Johnson et al. | 502/60 |
| 3,013,988 | 12/1961 | Bukata et al. | 502/79 |
| 3,367,885 | 2/1968 | Rabo et al. | 502/79 |
| 3,583,903 | 6/1971 | Miale et al. | 502/60 |
| 4,111,986 | 9/1978 | Zimmerschied | 562/549 |
| 4,271,311 | 6/1981 | Knickmeyer et al. | 560/86 |
| 4,492,773 | 1/1985 | Ball et al. | 518/715 |
| 4,694,097 | 9/1987 | Alper et al. | 502/24 |
| 4,822,825 | 4/1989 | Bhattacharya et al. | 518/714 |
| 5,006,496 | 4/1991 | Huixinga et al. | 502/61 |
| 5,010,049 | 4/1991 | Villa-Garcia et al. | 502/60 |
| 5,011,593 | 4/1991 | Ware et al. | 208/213 |
| 5,026,673 | 6/1991 | Gates et al. | 502/62 |
| 5,068,485 | 11/1991 | Iton et al. | 585/500 |

OTHER PUBLICATIONS

The Conversion of Methane to Higher Hydrocarbons Using Molybdenum-Sulfer Clusters Encapsulated in a Molecular Sieve, J. Pasterczyk, L. Iton, M. Winterer, T. Krause, T. Johnson, V. Maroni, Nov. 1991, pp. 1-8, DOE Contract No. W-31-109-Eng-38.

*Primary Examiner*—Carl F. Dees
*Attorney, Agent, or Firm*—Reinhart, Boerner, Van Deuren, Norris & Rieselbach

[57] ABSTRACT

A zeolite based catalyst for activation and conversion of methane. A zeolite support includes a transition metal (Mo, Cr or W) sulfide disposed within the micropores of the zeolite. The catalyst allows activation and conversion of methane to $C_{2+}$ hydrocarbons in a reducing atmosphere, thereby avoiding formation of oxides of carbon.

10 Claims, No Drawings

TRANSITION METAL SULFIDE LOADED CATALYST

This invention was made with Government support under Contract No. W-31-109-ENG-38 awarded by the Department of Energy. The Government has certain rights in this invention.

The present invention is concerned generally with the synthesis and use of a molecular sieve catalyst having selected transition metal sulfides disposed within pores of the molecular sieve crystals. More particularly, the invention is concerned with a zeolite-type molecular sieve having molybdenum, chromium or tungsten sulfide clusters disposed within the zeolite pores with the resulting catalyst operative under reducing conditions to directly convert methane to higher-level hydrocarbons.

Large economic benefits and substantial energy conservation could occur if larger fractions of fuels and high volume organic chemicals could be obtained from available resources rather than remote, unreliable sources. For example, in the United States there are sources of surplus natural gas, coal derived methane, highly-volatile coal derived chemicals and methanol. Substantial benefit could result if these resources could be converted to liquified petroleum gas, light olefins, gasoline range products, and various industrial intermediate products, such as xylenes, epoxides, aldehydes, and ketones. In the United States alone there are hundreds of trillions of cubic feet of excess methane gas associated with the coal reserves. The primary barrier to the use of these methane resources is the activation of the C—H bonds of methane to permit formation of higher molecular weight hydrocarbons ($C_2+$ hereinafter).

The goal of utilizing natural gas to produce fuels and large volume industrial chemicals is an old one, but little practical success has occurred to date. For example, steam reforming of natural gas to produce methanol is a workable process, but this methodology requires complex engineering steps, has a relatively inefficient thermodynamic energy balance, and requires a feedstock free of sulfur, chlorides, and other catalyst poisons. Similarly, the classic Fisher-Tropsch process has well known drawbacks, such as lack of product selectivity. Alternative methods have been developed, such as the Mobil Oil Company methanol-to-gasoline process. However, this process uses a particular shape selective molecular sieve catalyst which requires a feedstock of methanol or other functionalized light hydrocarbon and is not capable of directly inducing methane C—H activation. The Mobil approach therefore must use a front end conversion process, such as a steam reforming unit, to convert the methane feedstock to methanol. This type of process is a two-step method involving methane functionalization followed by controlled synthesis of higher molecular weight hydrocarbons. It would be highly advantageous to develop a catalytic process which would promote C—H activation in a manner that leads to direct conversion of methane to higher molecular weight hydrocarbons. As described in U.S. Pat. No. 5,068,485, which is incorporated by reference herein, a variety of well defined "designer" catalysts enable selective production of desired products (higher molecular weight hydrocarbons $C_2+$) from saturated, non-functionalized hydrocarbons reactants (methane, e.g.). Recent efforts to develop catalysts for direct conversion of methane to $C_2+$ hydrocarbons have emphasized the oxidative coupling reaction with oxygen. All catalysts to date demonstrating significant activity and selectivity in this reaction have been oxides or promoted metal oxides whose apparent mode of action is via the abstraction of hydrogen from $CH_4$ by oxygen ion defects, followed by gas phase coupling of the resulting $CH_3$ radicals. This type of methane reaction requires relatively high temperatures greater than about 950K. Oxidative coupling of methane is the generally favored mode of conversion because all direct methane coupling reactions are thermodynamically unfavorable, e.g.,

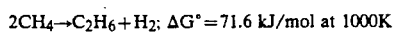
$$2CH_4 \rightarrow C_2H_6 + H_2; \ \Delta G^\circ = 71.6 \text{ kJ/mol at } 1000K$$

Oxidizing the eliminating hydrogen is required to render the reaction thermodynamically favorable:

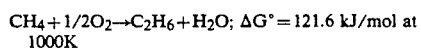
$$CH_4 + 1/2 O_2 \rightarrow C_2H_6 + H_2O; \ \Delta G^\circ = 121.6 \text{ kJ/mol at } 1000K$$

Deep oxidations of the hydrocarbons to oxides of carbon (carbon monoxide and carbon dioxide) are the undesirable competing reactions at the high operating temperatures and high oxygen activities used. Under these conditions an upper limit of about 20% conversion to $C_2$ hydrocarbons has been achieved using the best available catalysts. For economic feasibility such a direct process must yield a minimum of 25% selectivity of conversion of the $CH_4$ to $C_2+$ hydrocarbons under conditions where the total conversion of methane is near 100%.

Two mechanisms for the activation of methane C—H bonds by organometallic complexes have been elucidated, viz., (1) oxidative addition of $CH_4$ to naked 16-electron (coordinatively unsaturated) complex intermediates, e.g., $(C_5H_5)Ir(CO)$;, and (2) methyl group exchange in a four-center, four-electron transition state with electrophilic $d^0$ metal complexes, e.g., $(C_5H_5)_2Lu(CH_3)$. These reactions can be achieved at temperatures as low as 175K in solution or in the gas phase, but neither process leads to coupling reactions. We believe that encapsulating molybdenum sulfide clusters in zeolites can provide a high fraction of coordinatively unsaturated Mo ions by restricting the size of the clusters, and thereby catalytically useful methane coupling catalysts can be formulated from such clusters. Because use of air or oxygen to mediate oxidative methane coupling would result in the destructive oxidation of the sulfide encapsulate, the coupling reaction would have to be conducted in an alternative mode, in an essentially reducing environment. One possibility is to use a mixture of carbon monoxide and hydrogen as co-reactants since this also renders the coupling reaction thermodynamically favorable:

$$CH_4 + CO + 2H_2 \rightarrow C_2H_6 + H_2O; \ \Delta G^\circ < 0$$

Methane activation resulting in H/D exchange occurs at low temperature on metal surfaces (e.g., platinum), and dissociative chemisorption occurs at higher temperatures. The activity of unsupported platinum clusters in methane activation varies with the nuclearity of the cluster, is much higher for $Pt_2$ to $Pt_5$ than for larger clusters, and is very much higher for small clusters than for bulk platinum. Recent studies confirm that methane coupling can be accomplished at moderate temperatures by sequential exposure of a platinum catalyst to methane and hydrogen. We believe that catalysts can be formulated and processes devised whereby the activation of methane can be accomplished at modest temperatures, and its functionalization, or its coupling and homologation to higher hydrocarbons can be achieved in a non-oxidizing atmosphere.

It is therefore an object of the invention to provide a novel catalyst and method of use to induce C—H activation for production of $C_2+$ hydrocarbons from a reactant.

It is another object of the invention to provide an improved catalyst and method of use having transition metal sulfides disposed in a zeolite molecular sieve material.

It is a further object of the invention to provide a novel catalyst and method of use in a reducing atmosphere for conversion of methane to $C_2+$ hydrocarbons.

It is yet another object of the invention to provide an improved method of manufacture of a zeolite-based catalyst.

It is still a further object of the invention to provide a novel catalyst for activation of C—H bonds based on an H-Y or Na-Y zeolite having molybdenum, chromium and/or tungsten sulfide clusters disposed therein. Encapsulated mixed metal sulfide clusters of these transition elements are also preferred embodiments of this catalyst.

It is an additional object of the invention to provide a catalyst enabling C—H activation in a reducing atmosphere at low operating temperatures without production of oxides of carbon.

Other objects and advantages of the invention are set forth in the Detailed Description and Examples described below.

DETAILED DESCRIPTION OF PREFERRED EMBODIMENTS

In a preferred form of the invention a molecular sieve material is comprised of a zeolite (an aluminosilicate). Such materials have micropores of relatively uniform and predictable size in which metals and/or compounds and/or complexes of said metal can be disposed. These metal compound and/or complexes in the pores are surrounded by arrangements of silicon atoms, aluminum atoms and oxygen atoms. The unit cell size of a particular zeolite, such as zeolite H-Y or Na-Y, varies as the ratio of Si/Al. Such a unit cell structure defines internal cavities, including "super cages" and smaller sodalite cages accessible through relatively small pore apertures. A "super cage" size is typically on the molecular size range, such as small and large monomeric molecules and small oligomeric and polymeric molecules. For example, typical pore diameters are less than 2 nm diameter; and the more common pores are only 1 nm in diameter. Frequently, access to these pores is limited by the available access openings which are usually small since the large openings are relatively few in number. The zeolite structure itself can be modified as described in incorporated U.S. Pat. No. 5,068,485 or as described in U.S. Pat. No. 5,026,673 which is also incorporated by reference herein in its entirety.

In the case of the instant invention, H-Y and Na-Y zeolites were used to produce the desired catalyst. Other formulations of the zeolite host can be employed. Additional options include the Y-type zeolite ion exchanged with rare earth ions, or the hydrogen form of the zeolite beta, a more siliceous large pore zeolite that also has a three dimensional pore network.

Preparation of the encapsulated transition metal (Cr, Mo, and W) sulfur clusters described in the preferred embodiments requires the following four major steps: (1) preparation of the zeolite host matrix by ion exchange and/or calcination and evacuation; (2) adsorption of the transition metal into the zeolite micropores in the form of a monomeric complex precursor; (3) decomposition of the precursor complex to fix the transition metal ions in the pores of the molecular sieve matrix and (4) sulfidation of the transition metal ions.

The molecular sieves used as starting materials in the examples below were commercially available hydrated sodium-Y zeolite ($NaY \cdot H_2O$) and ammonium-Y zeolite ($NH_4Y \cdot H_2O$) powders (obtained from Strem Chemicals). The as-received Na-Y zeolite material (30g) was washed by stirring it in 3 liters 0.1M sodium chloride solution for 24 h at room temperature. The filtered zeolite was rinsed with ultrapure water, filtered and dried in a vacuum dessicator. Washed Na-Y zeolite or as-received $NH_4$-Y zeolite was calcined in a flow of dry air in a quartz tube, first heated at 425K for 12 h, then gradually heated to 725K and maintained for 12 h. This calcination procedure drives off ammonia from the $NH_4$-Y zeolite. The dry, carbon-free samples of Na-Y and H-Y zeolites produced were stored in a glove bag under argon or nitrogen for subsequent use. Air and water sensitivity of the chemicals and materials involved in these preparations require that all storage, as well as transferring and filling manipulations, be done in a glove bag under inert gas atmosphere. A quantity of 50g $MoCl_5$ was received in a sealed ampoule (Strem Chemicals) and was subdivided in an argon glovebox into 1 g portions in small ampoules which were subsequently sealed under vacuum.

Encapsulated molybdenum sulfur clusters within the pores of the zeolite were first prepared from $MoCl_5$ and H-Y zeolite according to the following scheme which serves as a prototype of the general procedure:

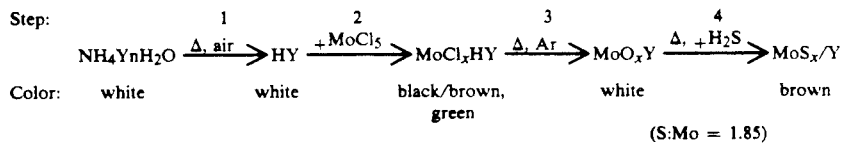

Step: 1     2     3     4

$NH_4YnH_2O \xrightarrow{\Delta, air} HY \xrightarrow{+MoCl_5} MoCl_xHY \xrightarrow{\Delta, Ar} MoO_xY \xrightarrow{\Delta, +H_2S} MoS_x/Y$ Color: white     white     black/brown, green     white     brown (S:Mo = 1.85)

Adsorption of $MoCl_5$ into the H-Y zeolite was performed in a sealed, evacuated ampoule. A portion of the zeolite was loaded at 350K to a level corresponding to 2 molecules of $MoCl_5$ per supercage (16 molecules per zeolite unit cell). This introduces enough pentavalent molybdenum to effect complete exchange of the $H^+$ ions in the parent H-Y zeolite, but induces loss of crystallinity in the solid state ion exchange process. The highest loss of crystallinity was found if the $MoCl_5$ was thoroughly premixed with HY powder in a mortar in glove bag under argon before sealing the mixture into the ampoule. Loss of crystallinity was reduced by sealing the H-Y zeolite (off-white) and the $MoCl_5$ (black) in the ampoule without premixing. This slows the MoCl$_5$ adsorption and the sealed evacuated ampoule was heated at 350K until the adsorption of the MoCl$_5$ was complete as judged visually by the formation of a brown product which subsequently changes color to green. To improve the homogeneity, the powders were mixed by occasional manual shaking of the ampoule during the heating process which lasted for several (up to 12) days. The H-Y zeolite loaded with the molybdenum chloride (MoCl$_x$/H-Y_ was stored in a glove bag under argon for subsequent use).

Solid state ion exchange of the zeolite with molybdenum was completed by heating a portion of the MoCl$_x$/H-Y material in flowing argon at 725K to effect the decomposition of the chloro complex intermediate. HCl is evolved in this step, and care is taken to avoid loss of volatile molybdenum species. This procedure yielded a white powder designated as MoO$_x$/H-Y which was stored in a glove bag under argon for subsequent use. A portion of this material was heated in flowing argon to 725K in a quartz tube then exposed to a slow flow of hydrogen sulfide gas. Progress of the sulfidation reaction was monitored by bubbling the effluent gas through acidic potassium permanganate and sodium hypochlorite solution in series. Upon decoloration of the permanganate solution, the H$_2$S flow was stopped; and the sample was purged with flowing argon at the reaction temperature for several hours to eliminate adsorbed unreacted excess hydrogen sulfide. The sample was cooled in flowing argon and transferred to an argon glove bag.

The Mo$_x$S$_y$ clusters were also produced from Mo(CO)$_6$ starting material using both H-Y and Na-Y zeolites as host material. The hexacarbonyl was adsorbed at 355K then decomposed in flowing air at about 720K. Sulfidation was performed using flowing H$_2$S at a temperature of 450K. This approach has also been used to generate encapsulated W$_x$S$_y$ and Cr$_x$S$_y$ clusters in zeolite from carbonyl precursors but with the calcination step done below 430K.

These product materials of Mo$_x$S$_y$ clusters in zeolite have been characterized by X-ray powder diffraction studies, chemical analysis, election paramagnetic resonance spectroscopy, in situ diffuse reflectance infrared Fourier transform (DRIFT hereinafter) spectroscopy, and X-ray absorption spectroscopy. Chemisorption of CO was evaluated by the DRIFT technique, and catalytic tests were performed using a conventional quartz flow microreactor in a closed loop recirculating system. The catalyst was exposed at 623K to a flowing hydrogen/methane (1:2) mixture diluted in helium, and condensible products were separated from the stream on each pass through the reactor by sending the stream through a sampling loop maintained at 77K (liquid N$_2$ boiling point). Example experimental data sets were also collected via sequential exposure of the catalyst to CH$_4$ and to H$_2$, and similar data were also accumulated for the reaction of CO with H$_2$.

Chemical evolution of the molybdenum processing examples were followed by examining H-Y zeolite after adsorption of MoCl$_5$. Electron paramagnetic resonance ("EPR" hereinafter) and extended X-ray adsorption fine structure ("EXAFS" hereinafter) data established that the molybdenum complex abstracts lattice oxygen upon adsorption at 350K. The complex was present as Mo$^V$O$_2$Cl at a loading of two complexes per supercage. Decomposition at 720K produced the fully oxidized monomeric Mo(VI) species. Clustering accompanied the sulfidation, producing a species identified from EXAFS as an incomplete cubane-type sulfur-bridged molybdenum (IV) cluster with the core being [Mo$_3$($\mu_3$-S)($\mu$-S)$_3$]. Clusters of this type are well known in the chemistry of molybdenum and tungsten. The EPR spectra established the presence of polymeric sulfur radicals formed in the zeolite as the Mo(VI) species is reduced. Upon exposure of the material to CO gas at 423K, chemisorbed CO was observed which exhibited a vibration at about 2,100 cm$^{-1}$, consistent with terminally bound CO. This establishes the accessibility of the clusters to adsorbates and confirms the coordinative unsaturation of the Mo ions in the cluster. Temperatures in excess of 473K were required to effect desorption/ decomposition of the chemisorbed CO. Similar clusters were obtained from the Mo(CO)$_6$ precursor adsorbed on either Na-Y or H-Y zeolite. The species obtained from W(CO)$_6$ on H-Y also exhibited strong CO chemisorption at 423K. The species obtained from Cr(CO)$_6$ on H-Y also chemisorbed CO at 423K, but two types of complexed CO were observed, of which only the minority type was strongly chemisorbed.

Treating the Mo$_3$S$_4$/H-Y material with CH$_4$ at 623K produced no methane coupling products nor evidence of adsorbed C—H fragments; however, subsequent exposure to H$_2$ yielded higher molecular weight hydrocarbons (C$_{2+}$). The absence of bound C—H fragments suggests that dehydrogenation is complete in the absence of added hydrogen. Catalytic tests using a 2:1 H$_2$:CH$_4$ mixture established that the Mo$_3$S$_4$/H-Y material produced primarily C$_2$ and C$_3$ alkanes and alkenes, with traces of C$_4$ and C$_5$ products. No oxides of carbon were produced.

The Mo$_3$S$_4$/H-Y catalyst maintained its methane coupling activity for many cycles over several months, with reactivation obtained by use of H$_2$ between runs. H$_2$S was a by-product in the early runs but gradually vanished. This is attributed to the hydrogenation of residual sulfur radical species (from the synthesis) and to extraction of sulfur from the [Mo$_3$S$_4$] cluster. For a catalyst prepared from Mo and S, chemical analysis established that the S:Mo ratio was depleted from 1.85 in the original catalyst to 0.33 in the material that had been extensively used in the reactor.

This Mo:S=3:1 ratio suggests that the depleted cluster has an [Mo$_3$S] type of core in which the three $\mu$-S ligands have been removed and the Mo ions reduced. EXAFS analysis of a sample reduced in H$_2$ at 723K confirmed the [Mo$_3$($\mu_3$-S)] core composition. Without limiting the scope of the invention, since the initial activity of the catalyst was maintained throughout, this suggests that the depleted cluster is itself active for methane activation. Whereas ethane was the Primary product of the methane coupling reaction on the molybdenum catalyst, propene is the primary product of the Fischer-Tropsch (CO+H$_2$) reaction on this catalyst at 623K.

The initial activity of the W$_x$S$_y$/H-Y catalyst was dramatically higher than that of Mo$_3$S$_4$/H-Y. Propene and benzene were the principal products of the reaction.

The following nonlimiting examples provide an illustration of the preparation of catalysts and their use.

EXAMPLES

Example 1

This example describes the preparation of encapsulated molybdenum sulfur clusters from $MoCl_5$ and H-Y zeolite. 1.268 g of anhydrous $MoCl_5$ and 3.94 g of the stored dry H-Y zeolite were mixed thoroughly in a mortar in a glove bag under argon. The homogeneous grey powder was transferred to a pyrex ampoule fitted with a stopcock. The ampoule was evacuated, sealed, and placed in an oven at 350K. The mixture began to change color to green at the bottom of the ampoule after 0.5 h, and was green after 16 h. The heating continued for 12 days with the ampoule wrapped in aluminium foil. The green powder was transferred in an argon glove bag to a quartz calcining tube equipped with a fritted disc. The material was heated to 430K in flowing argon over a period of 3 h. and held at this temperature for 33 h. The temperature was increased over a period of 2 h. and maintained at 690K for an additional 24 h. The white product was cooled in argon and stored in a glove bag under argon. For the sulfidation step this material was heated over a period of 4 h to 675K in flowing argon in the quartz calcining tube. The argon flow was maintained for an additional 3 h., then a slow flow of $H_2S$ was passed over the material with the temperature in the range 685–690 K. The effluent gas was bubbled through an acidified solution of potassium permanganate and a solution of sodium hypochlorite in series. Decoloration of the permanganate solution with precipitation of elemental sulfur indicated the completion of the sulfidation reaction after 20 mins of the $H_2S$ flow. The dark brown powder was cooled in flowing argon and transferred to an argon-filled glove bag for storage. The product contained 9.73 wt. % molybdenum and 6.01 wt. % sulfur. The X-ray powder diffraction pattern showed no evidence of an extraneous $MoS_2$ phase.

Example 2

This example describes the preparation of encapsulated molybdenum sulfur clusters from $MoCl_5$ and H-Y zeolite in a variant of Example 1. In an argon-filled glove bag, 4.490 g of the stored dry H-Y zeolite and 1.462 g of anhydrous $MoCl_5$ were placed, without mixing, in an ampoule fitted with a stopcock. The $MoCl_5$ formed the upper layer in the cylindical ampoule which was evacuated, sealed, and placed in an oven at 350K for 21 days. The resulting green powder was heated in flowing argon at 430K and cooled in flowing helium, then the white product was transferred to an argon-filled glove bag. For the sulfidation step this material was heated for 13 h. at 440K in flowing argon, then in a slow flow of $H_2S$ at this temperature for 10 min. The dark brown powder was cooled in flowing argon and transferred to an argon-filled glove bag for storage.

Example 3

This example describes the use of elemental sulfur for sulfidation of the molybdenum-containing zeolite. The green powder obtained by heating 0.444 g H-Y zeolite with 0.14 g $MoCl_5$ in a sealed ampoule at 358K for 14 days was heated in flowing argon for 20 h. at 550K, followed by 64 h. at 625K. Then, 0.308 g of the resulting white material was mixed with 0.015 g sulfur and sealed in an quartz ampoule after evacuation. The mixture was heated to 610K for 16 h., then the temperature was raised to 735K for 23 h. The product was a black material, and the X-ray powder diffraction pattern revealed the presence of a $MoS_2$ phase in addition to the zeolite.

Example 4

This example describes the preparation of encapsulated molybdenum sulfur clusters from molybdenum hexacarbonyl and Na-Y zeolite. In an argon-filled glove bag, 1.893 g of $Mo(CO)_6$ was placed in a cylindrical pyrex ampoule equipped with a stopcock. 5.761 g of the washed and dried Na-Y zeolite was added to the ampoule as a layer above the hexacarbonyl. The ampoule, wrapped in aluminium foil for protection from light, was evacuated and heated in an oven at 345K for 42 h., yielding a cream coloured product which was stored in an argon-filled glove bag. This $Mo(CO)_6$/Na-Y material was decomposed in flowing dry air with heating to 355K for 3 h., then to 600K for 5 h., and finally to 740K for 9 h. The resulting white powder was cooled in flowing air and transferred to an argon-filled glove bag. For the sulfidation step, the oxidized material was heated for 1 h. to 405K in flowing argon in the quartz calcining tube before changing to a slow flow of $H_2S$ for 1 h. Due to the exothermicity of the process, the temperature increased to 415K before returning to 405K. The dark brown product was purged at 405K with flowing argon for 1 h. before cooling and storing in an argon-filled glove bag. The product contained 9.04 wt. % molybdenum and 6.32 wt. % sulfur. The X-ray powder diffraction pattern showed no evidence of an extraneous $MoS_2$ phase.

Example 5

This example describes the preparation of encapsulated molybdenum sulfur clusters by direct sulfidation of molybdenum hexacarbonyl adsorbed in Na-Y zeolite. $Mo(CO)_6$/Na-Y, prepared in a manner similar to that described in example 4, was purged in flowing argon at room temperature (295K) for 1 h., then exposed to flowing $H_2S$. The temperature increased to 321K due to the exothermicity of the reaction. The flow of $H_2S$ was terminated after 15 min. The product was a light brown powder which contained 9.09 wt. % molybdenum and 1.10 wt. % sulfur.

Example 6

This example describes the preparation of encapsulated molybdenum sulfur clusters from molybdenum hexacarbonyl and Na-Y zeolite via a metallic cluster intermediate. A portion of the $Mo(CO)_6$/Na-Y used in Example 5 was heated in flowing argon. The temperature was held at 350K for 2 h., then gradually increased to 475K over a period of 3.5 h. The black product was cooled in flowing argon and stored in an argon-filled glove bag. For the sulfidation step, a portion of the black material was heated for 2 h. at 400K in flowing argon in the quartz calcining tube before changing to a slow flow of $H_2S$ for 0.5 h. Due to the exothermicity of the process, the temperature increased to 410K before returning to 03K. The black product was cooled in flowing argon and stored in an argon-filled glove bag.

Example 7

This example describes the preparation of encapsulated molybdenum sulfur clusters from molybdenum hexacarbonyl and H-Y zeolite. In an argon-filled glove bag, 0.922 g of $Mo(CO)_6$ was placed in a cylindrical pyrex ampoule equipped with a stopcock. Then, 2.514 g of the dried H-Y zeolite was added to the ampoule as a layer above the hexacarbonyl. The ampoule was evacuated using three freeze pump-thaw cycles then heated in an oven at 353K for 15 days. Some unadsorbed Mo(CO)$_6$ remained in the ampoule when this step was terminated. The Mo(CO)$_6$/Na-Y material was decomposed in flowing dry air with slow heating to 400K over 4 h. (the color changed to blue, then to grey), maintained at 400K for 6 h. (color changed to beige), and finally to 735K for 11 h. The resulting white powder was cooled in flowing argon to 446K, and then a slow flow of H$_2$S was admitted. The temperature quickly increased to 467K due to the exothermicity of the process, and the H$_2$S flow was terminated after 8 min. The product was cooled in flowing argon and stored in an argon-filled glove bag. The dark brown color was not entirely uniform throughout the powder.

Example 8

This example describes the preparation of encapsulated tungsten sulfur clusters from tungsten hexacarbonyl and Na-Y zeolite. In an argon-filled glove bag, 2.578 g of W(CO)$_6$ was placed in a cylindrical pyrex ampoule equipped with a stopcock. 5.835 g of the washed and dried Na-Y zeolite was added to the ampoule as a layer above the hexacarbonyl. The ampoule was evacuated and heated in an oven at 345K for 25 h., yielding a white product which was stored in an argon-filled glove bag. This W(CO)$_6$/Na-Y material was decomposed in flowing dry air with gradual heating to 780K over a period of 5 h., then maintained at 780K for an additional 14 h. The resulting white powder was cooled in flowing air to 310K, then heated in flowing argon to 415K over a period of 2 h. A slow flow of H$_2$S was passed over the material at this temperature for 15 min during which time the sample temperature increased to 424K. The yellow-brown product was purged with flowing argon at 453K for 1 h., then cooled in flowing argon and stored in an argon-filled glove bag. The color of this sample seemed to lighten after cooling, and it appeared to be particularly susceptible to oxidation. The product contained 15.2 wt. % tungsten and 1.05 wt. % sulfur.

Example 9

This example describes the preparation of encapsulated tungsten sulfur clusters by direct sulfidation of tungsten hexacarbonyl adsorbed in Na-Y zeolite. W(CO)$_6$/Na-Y, prepared in a manner similar to that described in Example 8, was purged in flowing argon at room temperature (296K) and then exposed to flowing H$_2$S for 5 min. The flow tube was wrapped in aluminium foil for protection from light during the procedure. The temperature increased to 308K due to the exothermicity of the reaction. The brown product was stored in an argon-filled glove bag.

Example 10

This example describes the preparation of encapsulated tungsten sulfur clusters from tungsten hexacarbonyl and H-Y zeolite. In an argon-filled glove bag, 1.583 g of W(CO)$_6$ was placed in a cylindical pyrex ampoule equipped with a stopcock. Then, 3.281 g of the dried H Y zeolite was added to the ampoule as a layer above the hexacarbonyl. The ampoule was evacuated using three freeze-pump-thaw cycles and heated in an oven at 358K for 48 h., yielding a white product which was stored in an argon-filled glove bag with an aluminium foil wrap for light protection. This W(CO)$_6$/H-Y material was decomposed in flowing dry air with gradual heating to 550K over a period of 23.5 h. The resulting white powder was cooled in flowing argon and stored in an argon-filled glove bag, then heated in flowing argon to 415K over a period of 2 h. A slow flow of H$_2$S was passed over the material at this temperature for 15 min during which time the sample temperature increased to 424K. The yellow-brown product was purged with flowing argon at 453K for 1 h., then cooled in flowing argon and stored in an argon-filled glove bag. A Schlenk apparatus was used for the sulfidation step because of the susceptibility of the tungsten materials to oxidation. The oxidized material was heated to 449K in flowing argon before changing to a slow flow of H$_2$S for 15 min. The temperature increased to 461K before returning to 448K. The deep red-brown product was cooled in flowing argon and stored in an argon-filled glove bag.

Example 11

This example describes the preparation of encapsulated chromium sulfur clusters from chromium hexacarbonyl and Na-Y zeolite. In an argon-filled glove bag, 1.944 g of Cr(CO)$_6$ was placed in a cylindrical pyrex ampoule equipped with a stopcock. 7.007 g of the washed and dried Na-Y zeolite was added to the ampoule as a layer above the hexacarbonyl. The ampoule, wrapped in aluminium foil for protection from light, was evacuated and heated in an oven at 353K for 24 h., yielding a beige coloured product which was stored in an argon-filled glove bag. This Cr(CO)$_6$/Na-Y material was decomposed in flowing dry air with heating to 750K over a period of 8 h., then maintained at 725K for an additional 15 h. The resulting thermochromic yellow-green powder was cooled in flowing air and transferred to an argon-filled glove bag. For the sulfidation step, the oxidized material was heated over a period of 4 h. to 464K in flowing argon in the quartz calcining tube before changing to a slow flow of H$_2$S for 10 min. The temperature increased to 468K during the reaction. The brown product was cooled in flowing argon and stored in an argon-filled glove bag. The product contained 4.58 wt. % chromium and 2.72 wt. % sulfur.

Example 12

This example describes the preparation of encapsulated chromium sulfur clusters from chromium hexacarbonyl and H-Y zeolite. In an argon-filled glove bag, 1.293 g of Cr(CO)$_6$ was placed in a cylindrical pyrex ampoule equipped with a stopcock. 4.544 g of the dried H-Y zeolite was added to the ampoule as a layer above the hexacarbonyl. The ampoule, wrapped in aluminium foil for protection from light, was evacuated using three freeze-pump-thaw cycles where only the bottom of the ampoule was submerged in the cryogen, such as liquid nitrogen. The ampoule was heated in an oven at 358K for 22 h., yielding a white Product. This Cr(CO)$_6$/H-Y material was decomposed in flowing dry air with rapid heating to 373K over a period of 10 min. The color changed to brown-green and a highly exothermic oxidation caused the temperature to jump to 429K then drop back to 388K. The material was maintained in flowing air at 399K for an additional 24 h. then was cooled in flowing argon and transferred to an argon-filled glove bag. For the sulfidation step, the oxidized material was heated over a period of 16 h. to 518K in flowing argon in the quartz calcining tube. The temperature was reduced to 440K and a slow flow of H$_2$S passed for 15 min. The temperature increased to 450K during the reaction then decreased. The brown-olive product was cooled in flowing argon and stored in an argon-filled glove bag.

Catalytic Results

The following examples detail representative results obtained in testing the catalytic activity of these zeolite-encapsulated transition metal sulfur cluster materials for methane conversion at moderate temperatures (<750K) and for carbon monoxide hydrogenation. The observed activity in both of these conversions indicates that these materials will also be active in catalyzing alkylation of alkenes and aromatics (and possibly alkanes) with methane, alkane dehydrogenation reactions, dehydrocyclization reactions, and hydrodesulfurization reactions, among others. The catalyst tests were conducted in a quartz flow reactor in a recirculating test system using about 800 torr helium as a carrier gas. The higher hydrocarbons and other condensible products were separated from the circulating gases in a trap maintained at 77K. After warming, the contents of the trap were analyzed using gas chromatography and gas chromatography-mass spectrometry. Since methane is not effectively trapped at 77K, the unreacted methane fraction is not accurately determined by this approach; and the $C_2+$ hydrocarbon distributions in the products constitute the salient results. Except for examples in which the feed gas mixture did not contain methane, the results in Table I show methane as N/A. The other product components are normalized with respect to their total carbon content.

Example 13

This example establishes that the $Mo_3S_4$/H-Y catalyst prepared using molybdenum pentachloride was not active for methane homologation in the absence of a second reactant. Approximately 0.5 g of fresh catalyst $Mo_3S_4$/H-Y, prepared as in Example 2, was loaded in the reactor under inert atmosphere (nitrogen) conditions. The reactor was inserted into the test system and evacuated for 30 min, then the catalyst was purged at room temperature in a flow (about 10ml/min) of UHP grade helium. The catalyst temperature was raised then maintained at 373K for 1 h, raised at 100°/h to 773K and maintained for 5 h. before cooling to 623K. The reactor and test system were loaded to a pressure of about 800 torr with helium (UHP) carrier gas, and the reactor was valved off from the rest of the test system manifold. 10 ml (STP) methane was introduced into the manifold, the product trap was cooled, and the He/CH$_4$ mixture was circulated at about 100 ml/min through the reactor for 1 h. Trace quantities of ethane and ethene were produced, and no CO$_2$ was detected, but H$_2$S was also formed.

Example 14

This example establishes that hydrogenation of the species retained on the $Mo_3S_4$/H-Y catalyst following exposure to pure methane yielded methane coupling products without deep oxidation. The $Mo_3S_4$/H-Y catalyst (Example 2) was treated with methane at 623K as in Example 13. It was then cooled to 523K and purged with UHP helium for 16 h. The temperature was returned to 623K and the experiment Performed with 20 ml(STP) hydrogen in the helium carrier gas circulating over the catalyst for 1 h. Small quantities of hydrocarbon products were obtained in the distribution shown in Table I. No carbon dioxide was produced, but H$_2$S was formed.

Example 15

This example establishes that the $Mo_3S_4$/H-Y catalyst prepared using molybdenum pentachloride effects methane coupling in the presence of hydrogen as a co-reactant at 673K without formation of oxides carbon. The $Mo_3S_4$/H-Y catalyst (Example 2) was cleaned of hydrocarbon or carbonaceous residues at 573K in a flow (8 ml/min) of 5% H$_2$ in He for 16 h. The reactor was then evacuated and the catalyst purged with flowing UHP helium. The catalyst was heated to 673K and exposed to a mixture of 10 ml (STP) methane and 20 ml (STP) hydrogen in the recirculating carrier gas for 1 h. The catalyst exhibited significant methane coupling activity in this hydrogen cofeeding mode yielding the product distribution shown in Table I. No carbon oxides were detected, but the conversion of methane is low, however. This catalyst exhibited the same activity for numerous catalyst test runs (applying the standard cleaning procedure between runs) throughout the period of 4 months for which it was kept in the reactor. The amount of H$_2$S formed in the tests decreased to zero with accumulated time of use, so that none was formed in most of the test runs. The hydrocarbon yield did not depend on the amount of H$_2$S by product. The sulfur content of the catalyst upon its removal from the reactor had been depleted from S:Mo=1.85 (atomic ratio) to S: Mo=0.33. The carbon present on the catalyst after a final exposure to methane corresponded to Mo :C>6.0 (atomic ratio).

Example 16

This example establishes that the $Mo_3S_4$/H-Y catalyst prepared using molybdenum pentachloride effects Fischer-Tropsch hydrogenation of carbon monoxide at 673K. The experiment described in Example 15 was repeated with the catalyst heated to 673K and exposed to a mixture of 10 ml(STP) carbon monoxide and 20 ml (STP) hydrogen in the recirculating carrier gas for 1 h. C$_3$ hydrocarbons predominant in the product as shown in Table I.

Example 17

This example establishes that the $Mo_3S_4$/H-Y catalyst prepared using molybdenum hexacarbonyl was not active for methane homologation in the absence of a second reactant. A procedure similar to that of Example 13 was repeated using fresh catalyst $Mo_3S_4$/H-Y, prepared as in Example 7. In this instance, the pretreatment in UHP helium was performed for 16 h. at 523K, followed by 7 h. at 623K. The result for the exposure of methane at 623K was the same as that found in Example 13.

EXAMPLE 18

This example establishes that hydrogenation of the species retained on the $Mo_3S_4$/H-Y catalyst (prepared using molybdenum hexacarbonyl) following exposure to pure methane yielded methane coupling products without deep oxidation. The experiment described in Example 14 was repeated for the $Mo_3S_4$/H-Y catalyst (Example 7). The result of the hydrogen exposure was the same as was found in Example 14.

Example 19

This example establishes that the $Mo_3S_4$/H-Y catalyst prepared using molybdenum hexacarbonyl effects methane coupling in the presence of hydrogen as a co-reactant at 673K without formation of oxides of carbon. The $Mo_3S_4$/H-Y catalyst (Example 7) was used in an experiment as described in Example 15. The activity and product distribution results were essentially the same as in Example 15. However, the activity of this catalyst was not sustained; it decreased substantially in only two weeks in the reactor.

Example 20

This example establishes that the unsulfided oxomolybdenum/H-Y catalyst prepared using molybdenum hexacarbonyl does not effect methane coupling in the presence of hydrogen as a co-reactant at 673K. The unsulfided product of the oxidation of $Mo(CO)_6$/H-Y (Example 7) was used as the catalyst in an experiment to convert the $CH_4/H_2$ mixture, similar to that described in Example 15. Negligible yields of higher hydrocarbon products were obtained. Sulfidation of the catalyst is the preferred embodiment.

Example 21

This example establishes that the $Mo_3S_4$/Na-Y catalyst prepared using molybdenum hexacarbonyl was not active for methane homologation in the absence of a second reactant. A procedure similar to that of Example 13 was repeated using fresh catalyst $Mo_3S_4$/Na-Y, prepared as in Example 4. In this instance, the pretreatment in UHP helium was performed for 16 h. at 423K, followed by cleaning in 5% $H_2$ in He for 28 h. at 623K. The result for the exposure of methane at 623K was the same as that found in Example 13.

Example 22

This example establishes that hydrogenation of the species retained on the $Mo_3S_4$/Na-Y catalyst (prepared using molybdenum hexacarbonyl) following exposure to pure methane yielded methane coupling products without deep oxidation. The experiment described in Example 14 was repeated for the $Mo_3S_4$/Na-Y catalyst (Example 4). The result of the hydrogen exposure was similar to that found in Example 14.

Example 23

This example establishes that the $Mo_3S_4$/Na-Y catalyst prepared using molybdenum hexacarbonyl effects methane coupling in the presence of hydrogen as a co-reactant at 673K without formation of oxides of carbon. The $Mo_3S_4$/Na-Y catalyst (Example 4) was used in an experiment as described in Example 15. The activity was only ≈50 % that of the $Mo_3S_4$/H-Y catalyst, but the product distribution results were similar to those found in Example 15. No carbon oxides were detected. The activity of this catalyst was not too sustained; it decreased rapidly in the course of a few test runs. The sulfur content of the catalyst upon its removal from the reactor had been depleted from S:Mo=2.09 (atomic ratio) to S:Mo=1.06. The carbon present on the catalyst after a final exposure to methane corresponded to Mo:C>11.0 (atomic ratio).

Example 24

This example establishes that the $W_xS_y$/H-Y catalyst prepared using tungsten hexacarbonyl effects methane coupling in the presence of hydrogen as a co-reactant at 673K without formation of oxides of carbon. The $W_xS_y$/H-Y catalyst (Example 10) was pretreated in the manner described in Example 13, but with the evacuation performed for consecutive 1 h. periods at 423K, 523K, and 623K, followed by 2 h. at 673K. The catalyst was then purged at 673K in flowing UHP helium (10ml/min) for 2 h., then cooled in the helium flow to 423K. The catalyst was then tested for conversion of the methane/hydrogen mixture at 623K as in Example 15. The initial activity was an order of magnitude greater than that found for the $Mo_3S_4$/H-Y catalyst The product distribution is shown in Table I and is quite different from that found for the $Mo_3S_4$/H-Y catalyst. The dominant product was propene, and benzene was among the other prominent Products However, the activity of this catalyst was not sustained; it decreased to about 10% of its initial value by the third run after the standard cleaning procedures between runs as described in example 15. The used catalyst contained 18.6 wt. % tungsten and 3.36 wt. % sulfur (S:W =1.04).

TABLE I

| Example No. | Carbon Content Ratio of Hydrocarbons | | | | | | | | |
|---|---|---|---|---|---|---|---|---|---|
| | $CH_4$ | $C_2H_4$ | $C_2H_6$ | $C_3H_4$ | $C_3H_6$ | $C_3H_8$ | $C_4$(total) | $C_4$(total) | $C_6H_6$ |
| 13 | N/A | tr | tr | — | — | — | — | — | — |
| 14 | 7 | 1 | 1 | — | 1 | tr | tr | — | — |
| 15 | N/A | 3 | 4 | — | 4 | 2 | tr | — | — |
| 16 | tr | tr | tr | — | 4 | 3 | — | — | — |
| 24 | N/A | 7 | 4 | 2 | 23 | 10 | (10) | $C_4 + C_5$ | 12 |

What is claimed is:

1. A catalyst for activation and conversion of methane, comprising:
   a zeolite support consisting of a material selected from the group consisting of H-Y zeolite, Na-Y zeolite, faujasite zeolite, rate earth ion exchanged Y-zeolite and hydrogen form of zeolite beta; and
   a transition metal sulfide cluster disposed within the pores of said zeolite support, said transition metal selected from the group consisting of Mo, Cr and W, said catalyst operative to activate methane under chemically reducing conditions.

2. The catalyst as defined in claim 1 wherein said Mo sulfide cluster is prepared from starting material selected from the group consisting of $MoCl_5$ and $Mo(CO)_6$ instilled in the pores of said zeolite support.

3. The catalyst as defined in claim 1 wherein said transition metal sulfide clusters are prepared from transition metal carbonyl precursors.

4. The catalyst as defined in claim 1 wherein said sulfide comprises $Mo_xS_y$ cluster with the ratio of x:y ranging from 0.75:1 to 3:1.

5. A catalyst able to activate methane for conversion to $C_2+$ hydrocarbons, comprising:
   a transition metal sulfide cluster disposed within a zeolite support, said transition metal selected from the group consisting of Mo, Cr and W and said transition metal sulfide operative under chemically reducing conditions to activate methane and convert said activated methane to said $C_2+$ hydrocarbons.

6. The catalyst as defined in claim 5 wherein said zeolite support is selected from the group consisting of H-Y zeolite, Na-Y zeolite, faujasite zeolite, rare earth ion exchanged Y-zeolite and hydrogen from of zeolite beta.

7. The catalyst as defined in claim 5 wherein said Mo sulfide consists essentially of $Mo_3S$. cluster.

8. The catalyst as defined in claim 5 wherein said transition metal cluster is a sulfidation product of hydrogen sulfide and a transition metal compound adsorbed in said zeolite support.

9. The catalyst as defined in claim 8 wherein said transition metal compound is selected from the group consisting of $MoCl_5$, $Mo(CO)_6$ and $MoO_2Cl$.

10. The catalyst as defined in claim 5 wherein said transition metal cluster is a sulfidation product of a transition metal carbonyl.

* * * * *

UNITED STATES PATENT AND TRADEMARK OFFICE
CERTIFICATE OF CORRECTION

PATENT NO. : 5,306,683

DATED : April 26, 1994

INVENTOR(S) : Victor A. Maroni et al.

It is certified that error appears in the above-identified patent and that said Letters Patent is hereby corrected as shown below:

| | |
|---|---|
| Column 6, Line 57, | cancel "Primary" and insert -- primary --; |
| Column 8, Line 60, | cancel "03K" and insert -- 403K --; |
| Column 9, Line 9, | cancel "$_6$h" and insert -- 6h --; |
| Column 9, Line 61, | cancel "cylindical" and insert -- cylindrical --; |
| Column 9, Lines 62-63, | cancel "H Y" and insert -- H-Y --; |
| Column 10, Line 56, | cancel "Product" and insert -- product --; |
| Column 11, Line 65, | cancel "Performed" and insert -- performed --; |
| Column 12, Line 8, | cancel "oxides" and insert -- oxide --; |
| Column 14, Line 46, | cancel "rate" and insert -- rare --; |
| Column 14, Lines 55-56, | cancel "$Mo(-CO)_6$" and insert -- $Mo(CO)_6$ --; |

UNITED STATES PATENT AND TRADEMARK OFFICE
CERTIFICATE OF CORRECTION

PATENT NO. : 5,306,683
DATED : April 26, 1994
INVENTOR(S) : Victor A. Maroni et al.

It is certified that error appears in the above-identified patent and that said Letters Patent is hereby corrected as shown below:

Column 14, Line 59, cancel "precusors" and insert -- precursors --;

Column 15, Line 11, cancel "$Mo_3S$." and insert -- $Mo_3S$ --.

Signed and Sealed this

Twentieth Day of September, 1994

*Attest:*

BRUCE LEHMAN

*Attesting Officer*  *Commissioner of Patents and Trademarks*